United States Patent
Mower

(12) 
(10) Patent No.: US 6,343,232 B1
(45) Date of Patent: *Jan. 29, 2002

(54) AUGMENTATION OF MUSCLE CONTRACTILITY BY BIPHASIC STIMULATION

(75) Inventor: Morton M. Mower, Baltimore, MD (US)

(73) Assignee: Mower CHF Treatment Irrevocable Trust, Baltimore, MD (US)

(*) Notice: Subject to any disclaimer, the term of this patent is extended or adjusted under 35 U.S.C. 154(b) by 0 days.

This patent is subject to a terminal disclaimer.

(21) Appl. No.: 09/692,409

(22) Filed: Oct. 19, 2000

Related U.S. Application Data

(63) Continuation-in-part of application No. 09/085,360, filed on May 27, 1998, now Pat. No. 6,141,587, which is a continuation-in-part of application No. 09/008,636, filed on Jan. 16, 1998, now Pat. No. 6,136,019, which is a continuation-in-part of application No. 08/699,552, filed on Aug. 19, 1966, now Pat. No. 5,871,506.

(51) Int. Cl.$^7$ ............................................... A61N 1/362
(52) U.S. Cl. ............................................ 607/9; 607/74
(58) Field of Search .......................... 607/9–11, 13–16, 607/68, 70, 74; 128/898

(56) References Cited

U.S. PATENT DOCUMENTS

| | | |
|---|---|---|
| 3,924,641 A | 12/1975 | Weiss |
| 3,946,745 A | 3/1976 | Siang-Lai et al. |
| 4,019,519 A | 4/1977 | Geerling |
| 4,055,190 A | 10/1977 | Tany |
| 4,222,386 A | 9/1980 | Smoknikov et al. ............ 607/9 |
| 4,233,986 A | 11/1980 | Tannenbaum |
| 4,298,007 A | 11/1981 | Wright et al. |
| 4,327,322 A | 4/1982 | Yukl |
| 4,343,312 A | 8/1982 | Cals et al. .................. 128/419 |

(List continued on next page.)

FOREIGN PATENT DOCUMENTS

| | | |
|---|---|---|
| EP | 0491649 A2 | 6/1992 |
| EP | 0600631 A2 | 11/1993 |
| EP | 0 491 649 B1 | 9/1996 |
| EP | 0 813 889 A2 | 12/1997 |
| EP | 0 850 662 | 7/1998 |
| EP | 0 870 516 | 10/1998 |
| EP | 0 600 631 | 12/1999 |
| FR | 2763247 | 11/1998 |
| WO | 93/01861 | 2/1993 |
| WO | 97/25098 | 7/1997 |

OTHER PUBLICATIONS

Guyton, Textbook of Medical Physiology, 8th Edition, Chapter 9, pp. 98–99, 1991.

(List continued on next page.)

Primary Examiner—Jeffrey R. Jastrzab
(74) Attorney, Agent, or Firm—Roberts Abokhair & Mardula, LLC

(57) ABSTRACT

Augmentation of electrical conduction and contractility by biphasic stimulation of muscle tissue. A first stimulation phase has a first phase polarity, amplitude, and duration. The first stimulation phase, which acts as a conditioning mechanism, is administered at no more than a maximum subthreshold amplitude. A second stimulation phase has a second polarity, amplitude, and duration. The two phases are applied sequentially. Contrary to current thought, anodal stimulation is applied as the first stimulation phase, followed by cathodal stimulation as the second stimulation phase. In this fashion, pulse conduction through muscle is improved, together with an increase in contractibility. Furthermore, this mode of biphasic stimulation reduces the electrical energy required to elicit contraction. In addition, the conditioning first stimulation phase decreases the stimulation threshold by reducing the amount of electrical current required for the second stimulation phase to elicit contraction. The muscle tissue encompassed by the present invention includes skeletal (striated) muscle, cardiac muscle, and smooth muscle.

10 Claims, 6 Drawing Sheets

U.S. PATENT DOCUMENTS

| | | |
|---|---|---|
| 4,392,496 A | 7/1983 | Stanton |
| 4,402,322 A | 9/1983 | Duggan |
| 4,429,697 A | 2/1984 | Nappholz et al. |
| 4,444,195 A | 4/1984 | Gold |
| 4,456,012 A | 6/1984 | Lattin |
| 4,498,478 A | 2/1985 | Bourgeois |
| 4,539,991 A | 9/1985 | Boute et al. |
| 4,543,956 A | 10/1985 | Herscovoci |
| 4,569,350 A | 2/1986 | Mumford et al. |
| RE32,091 E | 3/1986 | Stanton |
| 4,612,934 A | 9/1986 | Borkan |
| 4,637,397 A | 1/1987 | Jones et al. ............. 128/419 |
| 4,646,744 A | 3/1987 | Capel |
| 4,723,552 A | 2/1988 | Kenyon et al. |
| 4,754,759 A | 7/1988 | Allocca |
| 4,781,194 A | 11/1988 | Elmqvist |
| 4,821,724 A | 4/1989 | Whigham et al. ........... 607/13 |
| 4,823,810 A | 4/1989 | Dervieux |
| 4,875,484 A | 10/1989 | Anazi et al. |
| 4,903,700 A | 2/1990 | Whigham et al. ......... 128/419 |
| 4,919,140 A | 4/1990 | Borgens et al. |
| 4,924,880 A | 5/1990 | O'Neill et al. |
| 4,940,054 A | 7/1990 | Grevis et al. |
| 4,944,298 A | 7/1990 | Sholder |
| 4,976,264 A | 12/1990 | Petrofsky |
| 4,989,605 A | 2/1991 | Rossen |
| 4,996,987 A | 3/1991 | Peterofsky |
| 5,018,522 A | 5/1991 | Mehra ........................ 607/10 |
| 5,027,815 A | 7/1991 | Funke et al. |
| 5,036,850 A | 8/1991 | Owens |
| 5,048,522 A | 9/1991 | Petrofsky |
| 5,052,391 A | 10/1991 | Silberstone et al. |
| 5,058,584 A | 10/1991 | Bourgeois |
| 5,063,929 A | 11/1991 | Bartelt et al. |
| 5,065,083 A | 11/1991 | Owens |
| 5,069,211 A | 12/1991 | Bartelt et al. |
| 5,083,564 A | 1/1992 | Scherlag |
| 5,097,833 A | 3/1992 | Campos |
| 5,105,810 A | 4/1992 | Collins et al. |
| 5,109,847 A | 5/1992 | Liss et al. |
| 5,111,811 A | 5/1992 | Smits |
| 5,117,826 A | 6/1992 | Bartelt et al. |
| 5,163,429 A | 11/1992 | Cohen |
| 5,181,511 A | 1/1993 | Nickolls et al. |
| 5,193,535 A | 3/1993 | Bardy et al. |
| 5,209,229 A | 5/1993 | Gilli |
| 5,213,089 A | 5/1993 | Bennett et al. |
| 5,215,083 A | 6/1993 | Drane et al. |
| 5,224,475 A | 7/1993 | Berg et al. |
| 5,224,476 A | 7/1993 | Ideker et al. ............... 128/419 |
| 5,233,985 A | 8/1993 | Hudrlik |
| 5,300,096 A | 4/1994 | Hall et al. .................... 607/48 |
| 5,314,423 A | 5/1994 | Seney .......................... 606/20 |
| 5,314,495 A | 5/1994 | Kovacs ........................ 623/25 |
| 5,332,401 A | 7/1994 | Davey et al. ............... 607/116 |
| 5,334,220 A | 8/1994 | Sholder |
| 5,340,361 A | 8/1994 | Sholder |
| 5,350,401 A | 9/1994 | Levine |
| 5,391,185 A | 2/1995 | Kroll ............................. 607/4 |
| 5,411,525 A | 5/1995 | Swanson et al. ............... 607/5 |
| 5,411,547 A | 5/1995 | Causey, III ................. 607/129 |
| 5,421,830 A | 6/1995 | Epstein et al. ................ 607/30 |
| 5,422,525 A | 6/1995 | Mansir |
| 5,423,868 A | 6/1995 | Nappholz et al. |
| 5,441,522 A | 8/1995 | Schuller |
| 5,458,625 A | 10/1995 | Kendall ........................ 607/46 |
| 5,468,254 A | 11/1995 | Hahn et al. .................... 607/5 |
| 5,480,413 A | 1/1996 | Greenhut et al. ............. 607/14 |
| 5,487,759 A | 1/1996 | Bastyr et al. ................ 607/149 |
| 5,507,781 A | 4/1996 | Kroll et al. ..................... 607/7 |
| 5,514,161 A | 5/1996 | Limousin ........................ 607/9 |
| 5,514,163 A | 5/1996 | Markowitz et al. |
| 5,522,858 A | 6/1996 | van der Veen ............... 607/14 |
| 5,527,347 A | 6/1996 | Shelton et al. |
| 5,534,015 A | 7/1996 | Kroll et al. ..................... 607/7 |
| 5,534,018 A | 7/1996 | Wahlstrand et al. .......... 607/27 |
| 5,545,186 A | 8/1996 | Olson et al. |
| 5,562,708 A | 10/1996 | Combs et al. .................. 607/4 |
| 5,601,608 A | 2/1997 | Mouchawar .................... 607/5 |
| 5,620,470 A | 4/1997 | Gliner et al. ................... 607/5 |
| 5,620,471 A | 4/1997 | Duncan ....................... 607/14 |
| 5,626,620 A | 5/1997 | Kieval et al. |
| 5,649,966 A | 7/1997 | Noren et al. ................... 607/4 |
| 5,662,698 A | 9/1997 | Altman et al. .............. 607/123 |
| 5,713,929 A | 2/1998 | Hess et al. .................... 607/14 |
| 5,718,720 A | 2/1998 | Prutchi et al. |
| 5,735,876 A | 4/1998 | Kroll et al. |
| 5,741,303 A | 4/1998 | Kroll et al. ..................... 607/5 |
| 5,800,465 A | 9/1998 | Thompson et al. ............ 607/9 |
| 5,814,079 A | 9/1998 | Kieval ........................... 607/4 |
| 5,855,592 A | 1/1999 | McGee et al. |
| 5,855,594 A | 1/1999 | Olive et al. |
| 5,871,506 A | 2/1999 | Mower .......................... 607/9 |
| 5,968,081 A | 10/1999 | Levine .......................... 607/9 |
| 6,067,470 A | 5/2000 | Mower .......................... 607/5 |
| 6,136,019 A | 10/2000 | Mower .......................... 607/9 |
| 6,141,586 A | 10/2000 | Mower .......................... 607/9 |
| 6,141,587 A * | 10/2000 | Mower .......................... 607/9 |
| 6,178,351 B1 | 1/2001 | Mower .......................... 607/5 |

OTHER PUBLICATIONS

Brian G. Cleland, "A Conceptual Basis for Pacing Waveforms," Pace, vol. 19, 1177–1185 (Aug. 1996).

Allen M. Greenspan, M.D., "Electrophysiology of Pacing," 29–35, Ideal Cardiac Pacing, vol. 37 in the Series, Major Problems in Clinical Surgey (1984).

Brian F. Hoffman, M.D., and Paul F. Carnefield, M.D., Electrophysiology of the Heart, 220–222 (1976).

Bradley J. Roth, Ph.D., "Strength–Internal Curves for Cardiac Tissue Predicted Using the Bidomain Model," Journal of Cardiovascular Electrophysiology, vol. 7, No. 8, 722–737 (Aug. 1996).

Harold Siddons and Edgar Sowton, "Cardiac Pacemakers," 152–154.

Estes et al., Implantable Cardioverter–Defibrillators, p. 181 (1994).

Ravazzi et al., Changes Induced in Ventricular Activator Using Non–Standard Pacing Pulse Morphologies at Different Right Septal Sires (1998).

Ravazzi et al., Ventricular Pacing Threshold Improvement Using Non–Standard Pacing Pulse Morphologies at Different Right Septal Sites (1998).

Prochaczek et al., Transcutaneous Ventricular Pacing of the Human Heart with Increased Overthreshold Energy; Hemodynamic Effects (1998).

Kutarski et al., Cathode or Anode in Coronary Sinus (CS) in Pts With Daubert's BiA Pacing System (1998).

* cited by examiner

AUGMENTATION OF MUSCLE CONTRACTILITY BY BIPHASIC STIMULATION

CROSS REFERENCE TO RELATED APPLICATIONS

This application is a continuation-in-part of the U.S. patent application Ser. No. 09/085,360, filed May 27, 1998, now U.S. Pat. No. 6,141,587, which is a continuation-in-part application of the U.S. patent application Ser. No. 09/008, 636, filed Jan. 16, 1998, now U.S. Pat. No. 6,136,019, which is a continuation-in-part application of the U.S. patent application Ser. No. 08/699,552, filed Aug. 19, 1996, now U.S. Pat. No. 5,871,506. The Ser. Nos. 09/085,360, 09/008, 636, and 08/699,552 applications, as well as the U.S. Pat. No. 5,871,506, are all incorporated by reference herein, in their entirety, for all purposes.

BACKGROUND OF THE INVENTION

1. Field of the Invention

This invention relates generally to a method for the stimulation of muscle tissue. In particular, this invention relates to a method for stimulation of muscle tissue with biphasic waveforms that reduce the electrical energy required to elicit contraction.

2. Background Information

The function of the cardiovascular system is vital for survival. Through blood circulation, body tissues obtain necessary nutrients and oxygen, and discard waste substances. In the absence of circulation, cells begin to undergo irreversible changes that lead to death. The muscular contractions of the heart are the driving force behind circulation.

In cardiac muscle, the muscle fibers are interconnected in branching networks that spread in all directions through the heart. When any portion of this net is stimulated, a depolarization wave passes to all of its parts and the entire structure contracts as a unit. Before a muscle fiber can be stimulated to contract, its membrane must be polarized. A muscle fiber generally remains polarized until it is stimulated by some change in its environment. A membrane can be stimulated electrically, chemically, mechanically or by temperature change. The minimal stimulation strength needed to elicit a contraction is known as the threshold stimulus. The maximum stimulation amplitude that may be administered without eliciting a contraction is the maximum subthreshold amplitude.

Where the membrane is stimulated electrically, the impulse amplitude required to elicit a response is dependent upon a number of factors. First, is the duration of current flow. Since the total charge transferred is equal to the current amplitude times the pulse duration, increased stimulus duration is associated with a decrease in threshold current amplitude. Second, the percentage of applied current that actually traverses the membrane varies inversely with electrode size. Third, the percentage of applied current that actually traverses the membrane varies directly with the proximity of the electrode to the tissue. Fourth, the impulse amplitude required to elicit a response is dependent upon the timing of stimulation within the excitability cycle.

Throughout much of the heart are clumps and strands of specialized cardiac muscle tissue. This tissue comprises the cardiac conduction system and serves to initiate and distribute depolarization waves throughout the myocardium. Any interference or block in cardiac impulse conduction may cause an arrhythmia or marked change in the rate or rhythm of the heart Sometimes a patient suffering from a conduction disorder can be helped by an artificial pacemaker. Such a device contains a small battery powered electrical stimulator. When the artificial pacemaker is installed, electrodes are generally threaded through veins into the right ventricle, or into the right atrium and right ventricle, and the stimulator is planted beneath the skin in the shoulder or abdomen. The leads are planted in intimate contact with the cardiac tissue. The pacemaker then transmits rhythmic electrical impulses to the heart, and the myocardium responds by contracting rhythmically. Implantable medical devices for the pacing of the heart are well known in the art and have been used in humans since approximately the mid 1960s.

Either cathodal or anodal current may be used to stimulate the myocardium. However anodal current is thought not to be useful clinically. Cathodal current comprises electrical pulses of negative polarity. This type of current depolarizes the cell membrane by discharging the membrane capacitor, and directly reduces the membrane potential toward threshold level. Cathodal current, by directly reducing the resting membrane potential toward threshold, has a one-half to one-third lower threshold current in late diastole than does anodal current. Anodal current comprises electrical pulses of positive polarity. The effect of anodal current is to hyperpolarize the resting membrane. On sudden termination of the anodal pulse, the membrane potential returns towards resting level, overshoots to threshold, and a propagated response occurs. The use of anodal current to stimulate the myocardium is generally discouraged due to the higher stimulation threshold, which leads to use of a higher current, resulting in a drain on the battery of an implanted device and impaired longevity. Additionally, the use of anodal current for cardiac stimulation is discouraged due to the suspicion that the anodal contribution to depolarization can, particularly at higher voltages, contribute to arrhythmogenesis.

Virtually all artificial pacemaking is done using stimulating pulses of negative polarity, or in the case of bipolar systems, the cathode is closer to the myocardium than is the anode. Where the use of anodal current is disclosed, it is generally as a charge of minute magnitude used to dissipate residual charge on the electrode. This does not affect or condition the myocardium itself. For additional details, refer to the disclosure of U.S. Pat. No. 4,543,956 to Herscovici.

In using a triphasic waveform, the first and third phases have nothing to do with the myocardium per se, but are only envisioned to affect the electrode surface itself Thus, the charge applied in these phases is of very low amplitude. Disclosures relevant to this practice are found in U.S. Pat. Nos. 4,903,700 and 4,821,724 to Whigham et al., and 4,343,312 to Cals et al.

Lastly, biphasic stimulation has been used to produce voltage doubling without the need for a large capacitor in the output circuit. The phases of the biphasic stimulation disclosed are of equal magnitude and duration. Refer to U.S. Pat. No. 4,402,322 to Duggan for details.

What is needed is an improved means for stimulating muscle tissue, wherein the contraction elicited is enhanced and the damage to the tissue adjacent to the electrode is diminished.

Enhanced myocardial function is obtained through the biphasic pacing of the present invention. The combination of cathodal with anodal pulses of either a stimulating or conditioning nature, preserves the improved conduction and contractility of anodal pacing while eliminating the drawback of increased stimulation threshold. The result is a depolarization wave of increased propagation speed. This increased propagation speed results in superior cardiac contraction leading to an improvement in blood flow. Improved stimulation at a lower voltage level also results in reduction in power consumption and increased life for pacemaker batteries.

As with the cardiac muscle, striated muscle may also be stimulated electrically, chemically, mechanically or by temperature change. Where the muscle fiber is stimulated by a motor neuron, the neuron transmits an impulse that activates all of the muscle fibers within its control, that is, those muscle fibers in its motor unit. Depolarization in one region of the membrane stimulates adjacent regions to depolarize as well, resulting in a wave of depolarization traveling over the membrane in all directions away from the site of stimulation. Thus, when a motor neuron transmits an impulse, all the muscle fibers in its motor unit are stimulated to contract simultaneously.

The minimum strength to elicit a contraction is called the threshold stimulus. Once this level of stimulation has been met, the generally held belief is that increasing the level will not increase the contraction. Additionally, since the muscle fibers within each muscle are organized into motor units, and each motor unit is controlled by a single motor neuron, all of the muscle fibers in a motor unit are stimulated at the same time. However, the whole muscle is controlled by many different motor units that respond to different stimulation thresholds. Thus, when a given stimulus is applied to a muscle, some motor units may respond while others may not.

The combination of cathodal and anodal pulses of the present invention also provides improved contraction of striated muscle where electrical muscular stimulation is indicated due to neural or muscular damage. Where nerve fibers have been damaged due to trauma or disease, muscle fibers in the regions supplied by the damaged nerve fiber tend to undergo atrophy and waste away. A muscle that cannot be exercised may decrease to half of its usual size in a few months. Where there is no stimulation, not only will the muscle fibers decrease in size, but they will become fragmented and degenerated, and replaced by connective tissue. Through electrical stimulation, one may maintain muscle tone such that, upon healing or regeneration of the nerve fiber, viable muscle tissue remains, and the overall regenerative process is thereby enhanced and assisted.

Striated muscle stimulation can also serve to preserve the neural pathway, such that, upon healing of the nerve fibers associated with the stimulated tissue, the patient "remembers" how to contract that particular muscle. Enhanced striated muscle contraction is obtained through the biphasic stimulation of the present invention. The combination of cathodal with anodal pulses of either a stimulating or conditioning nature results in contraction of a greater number of motor units at a lower voltage level, leading to superior muscle response.

Lastly, biphasic stimulation as provided by the present invention may be desirable to stimulate smooth muscle tissue, such as those muscles responsible for the movements that force food through the digestive tube, constrict blood vessels and empty the urinary bladder. For example, appropriate stimulation could rectify the difficulties associated with incontinence.

SUMMARY OF THE INVENTION

It is therefore an object of the present invention to provide improved electrical stimulation of muscle tissue.

It is another object of the present invention to extend battery life of implantable electrical stimulation devices.

It is a further object of the present invention to obtain effective muscle stimulation at a lower voltage level.

It is a further object of the present invention to provide improved stimulation of muscle tissue, particularly striated muscle.

It is a further object of the present invention to provide contraction of a greater number of muscle motor units at a lower voltage level.

It is a further object of the present invention to provide contraction of a greater number of muscle motor units at a lower level of electrical current.

A method and apparatus for muscular stimulation in accordance with the present invention includes the administration of biphasic stimulation to the muscle tissue, wherein both cathodal and anodal pulses are administered.

According to a still further aspect of this invention, the stimulation is administered to muscle tissue to evoke muscular response. Stimulation may be administered directly or indirectly to muscle tissue, where indirect administration includes stimulation through the skin. Using the present invention, lower levels of electrical energy (voltage and/or current) are needed to reach the threshold stimulus, compared to conventional stimulation methods. Muscle tissues that may benefit from stimulation according to the present invention include skeletal (striated) muscle, cardiac muscle, and smooth muscle.

The electronics required for the implantable stimulation devices needed to practice the method of the present invention are well known to those skilled in the art. Current implantable stimulation devices are capable of being programmed to deliver a variety of pulses, including those disclosed herein. In addition, the electronics required for indirect muscle stimulation are also well known to those skilled in the art and are readily modified to practice the method of the present invention.

The method and apparatus of the present invention comprises a first and second stimulation phase, with each stimulation phase having a polarity, amplitude, shape, and duration. In a preferred embodiment, the first and second phases have differing polarities. In one alternative embodiment, the two phases are of differing amplitude. According to a second, alternate embodiment, the two phases are of differing duration. According to a third, alternate embodiment, the first phase is in a chopped waveform. According to a fourth, alternate embodiment, the amplitude of the first phase is ramped.

Preferably the invention is embodied such that the first phase of stimulation is an anodal pulse at maximum sub-threshold amplitude for a long duration, and the second phase of stimulation is a cathodal pulse of short duration and high amplitude. It is noted that the aforementioned alternate embodiments can be combined in differing fashions. These alternate embodiments are presented by way of example only, and are not intended to be limiting.

BRIEF DESCRIPTION OF THE DRAWINGS

Additional objects and advantages of the present invention will be apparent in the following detailed description read in conjunction with the accompanying drawing figures.

DETAILED DESCRIPTION OF THE INVENTION

Figure 1:
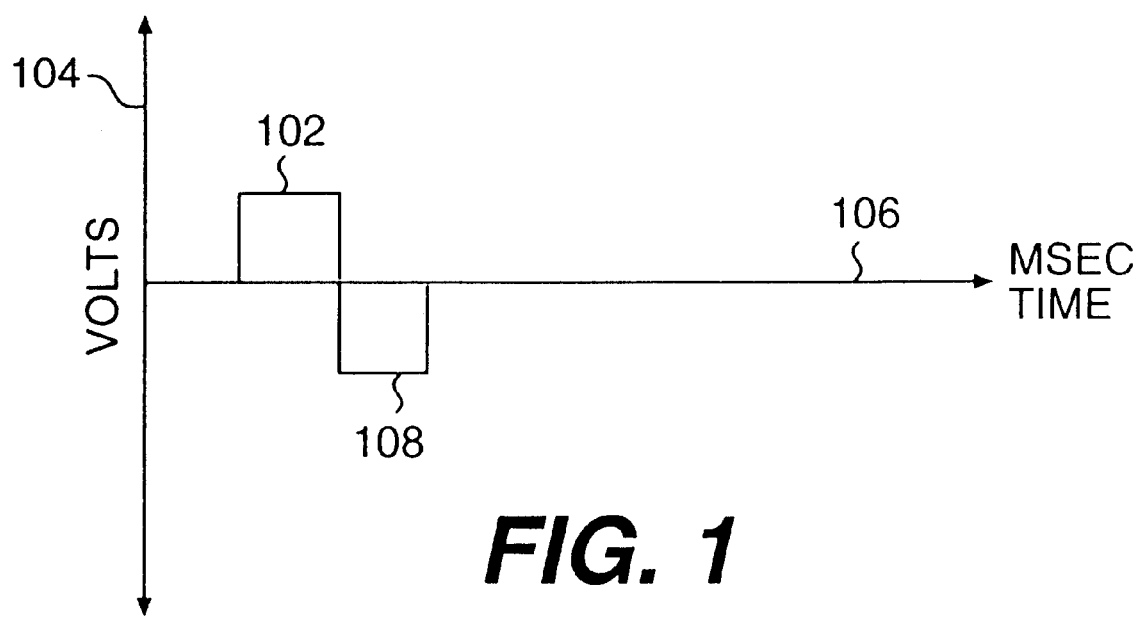
FIG. 1 is a schematic representation of leading anodal biphasic stimulation.

The present invention relates to the biphasic electrical stimulation of muscle tissue. FIG. 1 depicts biphasic electrical stimulation wherein a first stimulation phase, comprising anodal stimulus 102, is administered having amplitude 104 and duration 106. This first stimulation phase is immediately followed by a second stimulation phase comprising cathodal stimulation 108 of equal intensity and duration.

Figure 2:
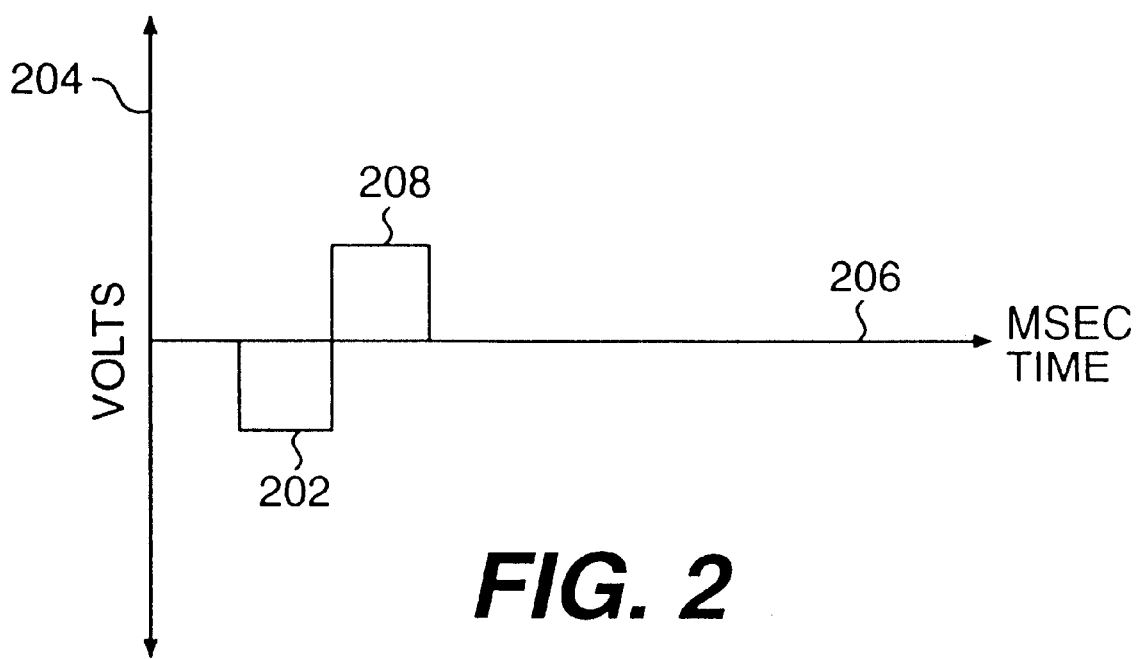
FIG. 2 is a schematic representation of leading cathodal biphasic stimulation.

FIG. 2 depicts biphasic electrical stimulation wherein a first stimulation phase, comprising cathodal stimulation 202 having amplitude 204 and duration 206, is administered. This first stimulation phase is immediately followed by a second stimulation phase comprising anodal stimulation 208 of equal intensity and duration.

Figure 3:
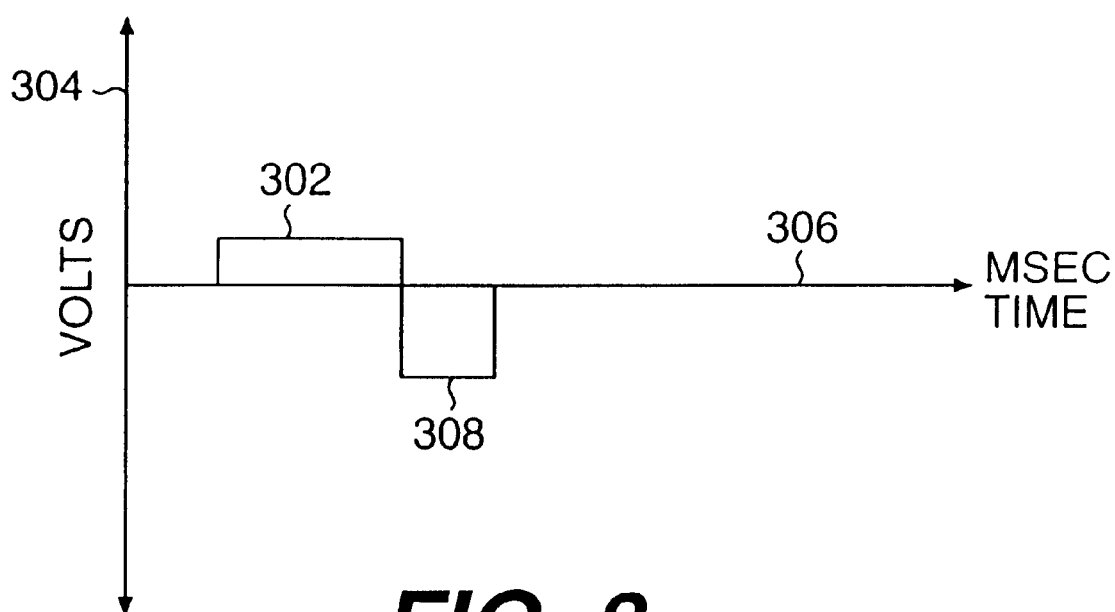
FIG. 3 is a schematic representation of leading anodal stimulation of low level and long duration, followed by conventional cathodal stimulation.

FIG. 3 depicts a preferred embodiment of the present invention wherein a first stimulation phase, comprising low level, long duration anodal stimulation 302 having amplitude 304 and duration 306, is administered. This first stimulation phase is immediately followed by a second stimulation phase comprising cathodal stimulation 308 of conventional intensity and duration. In an alternative embodiment of the invention, anodal stimulation 302 is at maximum subthreshold amplitude. In yet another alternative embodiment of the invention, anodal stimulation 302 is less than three volts. In another alternative embodiment of the invention, anodal stimulation 302 is a duration of approximately two to eight milliseconds. In yet another alternative embodiment of the invention, cathodal stimulation 308 is of a short duration. In another alternative embodiment of the invention, cathodal stimulation 308 is approximately 0.3 to 0.8 millisecond. In yet another alternative embodiment of the invention, cathodal stimulation 308 is of a high amplitude. In another alternative embodiment of the invention, cathodal stimulation 308 is in the approximate range of three to twenty volts. In yet another alternative embodiment of the present invention, cathodal stimulation 308 is of a duration less than 0.3 millisecond and at a voltage greater than twenty volts. In another alternative embodiment of the present invention, cathodal stimulation 308 lasts as long as 6.0 milliseconds and has a voltage as low as 200 millivolts. In the manner disclosed by these embodiments, as well as those alterations and modifications that may become obvious upon the reading of this specification, a maximum membrane potential without activation is achieved in the first phase of stimulation.

Figure 4:
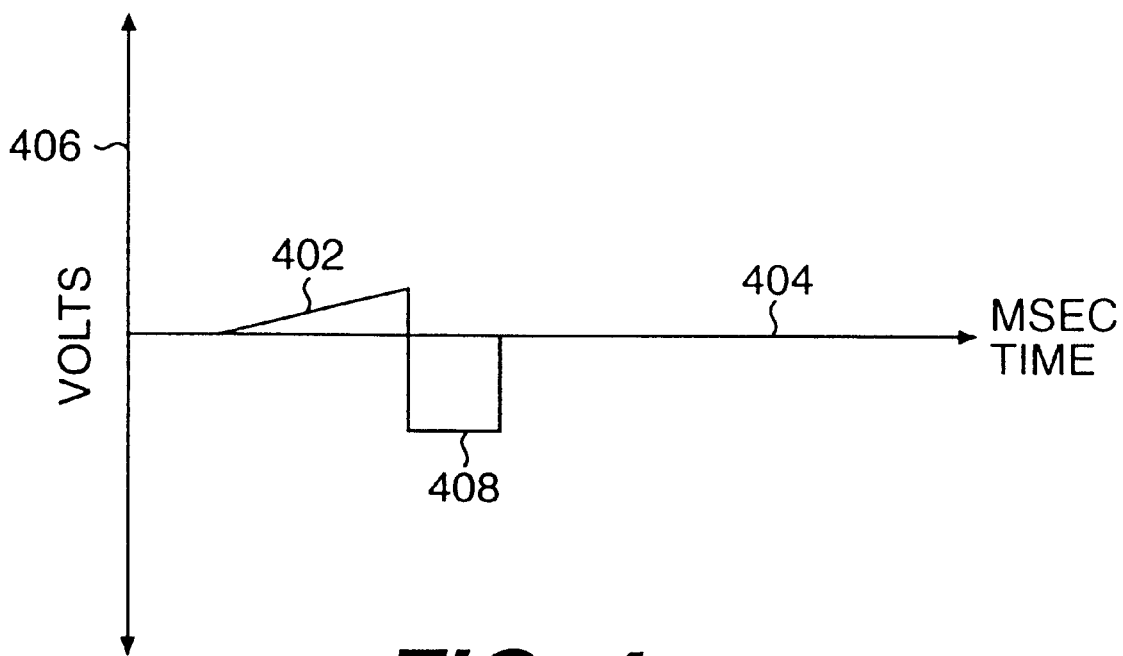
FIG. 4 is a schematic representation of leading anodal stimulation of ramped low level and long duration, followed by conventional cathodal stimulation.

FIG. 4 depicts an alternative preferred embodiment of the present invention wherein a first stimulation phase, comprising anodal stimulation 402, is administered over period 404 with rising intensity level 406. The ramp of rising intensity level 406 may be linear or non-linear, and the slope may vary. This anodal stimulation is immediately followed by a second stimulation phase comprising cathodal stimulation 408 of conventional intensity and duration. In an alternative embodiment of the invention, anodal stimulation 402 rises to a maximum subthreshold amplitude. In yet another alternative embodiment of the invention, anodal stimulation 402 rises to a maximum amplitude that is less than three volts. In another alternative embodiment of the invention, anodal stimulation 402 is a duration of approximately two to eight milliseconds. In yet another alternative embodiment of the invention, cathodal stimulation 408 is of a short duration. In another alternative embodiment of the invention, cathodal stimulation 408 is approximately 0.3 to 0.8 millisecond. In yet another alternative embodiment of the invention, cathodal stimulation 408 is of a high amplitude. In another alternative embodiment of the invention, cathodal stimulation 408 is in the approximate range of three to twenty volts. In yet another alternative embodiment of the present invention, cathodal stimulation 408 is of a duration less than 0.3 milliseconds and at a voltage greater than twenty volts. In another alternative embodiment of the present invention, cathodal stimulation 408 lasts as long as 6.0 milliseconds and has a voltage as low as 200 millivolts. In the manner disclosed by these embodiments, as well as those alterations and modifications that may become obvious upon the reading of this specification, a maximum membrane potential without activation is achieved in the first phase of stimulation.

Figure 5:
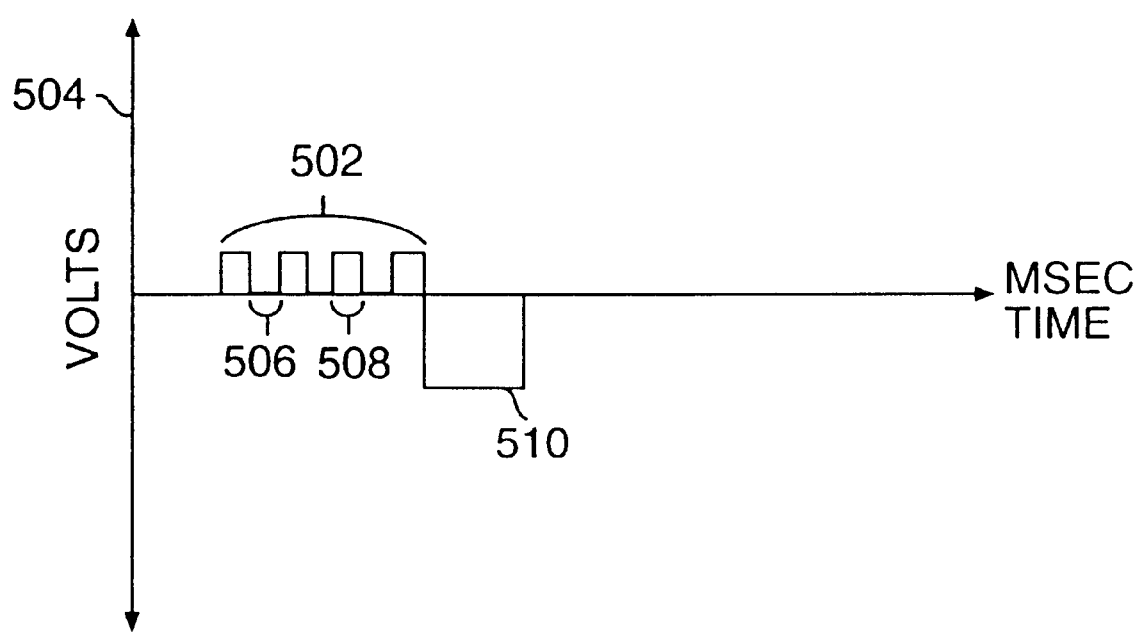
FIG. 5 is a schematic representation of leading anodal stimulation of low level and short duration, administered in series, followed by conventional cathodal stimulation.

FIG. 5 depicts biphasic electrical stimulation wherein a first stimulation phase, comprising series 502 of anodal pulses, is administered at amplitude 504. In one embodiment, rest period 506 is of equal duration to stimulation period 508, and is administered at baseline amplitude. In an alternative embodiment, rest period 506 is of a differing duration than stimulation period 508 and is administered at baseline amplitude. Rest period 506 occurs after each stimulation period 508, with the exception that a second stimulation phase, comprising cathodal stimulation 510 of conventional intensity and duration, immediately follows the completion of series 502. In an alternative embodiment of the invention, the total charge transferred through series 502 of anodal stimulation is at the maximum subthreshold level. In another alternative embodiment of the invention, cathodal stimulation 510 is of a short duration. In yet another alternative embodiment of the invention, cathodal stimulation 510 is approximately 0.3 to 0.8 millisecond. In another alternative embodiment of the invention, cathodal stimulation 510 is of a high amplitude. In yet another alternative embodiment of the invention, cathodal stimulation 510 is in the approximate range of three to twenty volts. In another alternative embodiment of the invention, cathodal stimulation 510 is of a duration less than 0.3 millisecond and at a voltage greater than twenty volts. In another alternative embodiment of the present invention, cathodal stimulation 510 lasts as long as 6.0 milliseconds and has a voltage as low as 200 millivolts.

EXAMPLE 1

Stimulation and propagation characteristics of the myocardium were studied in isolated hearts using pulses of differing polarities and phases. The experiments were carried out in five isolated Langendorff perfused rabbit hearts. Conduction velocity on the epicardium was measured using an array of bipolar electrodes. Measurements were made between six millimeters and nine millimeters from the stimulation site. Transmembrane potential was recorded using a floating intracellular microelectrode. The following protocols were examined: monophasic cathodal pulse, monophasic anodal pulse, leading cathodal biphasic pulse, and leading anodal biphasic pulse.

Table 1 discloses the conduction speed transverse to fiber direction for each stimulation protocol administered, with stimulations of three, four and five volts and two millisecond pulse duration.

TABLE 1

| Conduction Speed Transverse to Fiber Direction, 2 msec duration | | |
| --- | --- | --- |
| 3 V | 4 V | 5 V |
| Cathodal Monophasic | | |
| 18.9 ± 2.5 cm/sec | 21.4 ± 2.6 cm/sec | 23.3 ± 3.0 cm/sec |
| Anodal Monophasic | | |
| 24.0 ± 2.3 cm/sec | 27.5 ± 2.1 cm/sec | 31.3 ± 1.7 cm/sec |
| Leading Cathodal Biphasic | | |
| 27.1 ± 1.2 cm/sec | 28.2 ± 2.3 cm/sec | 27.5 ± 1.8 cm/sec |
| Leading Anodal Biphasic | | |
| 26.8 ± 2.1 cm/sec | 28.5 ± 0.7 cm/sec | 29.7 ± 1.8 cm/sec |

Table 2 discloses the conduction speed along fiber direction for each stimulation protocol administered, with stimulations of three, four and five volts and two millisecond pulse duration.

TABLE 2

| Conduction Speed Along Fiber Direction, 2 msec stimulation | | |
| --- | --- | --- |
| 3 V | 4 V | 5 V |
| Cathodal Monophasic | | |
| 45.3 ± 0.9 cm/sec | 47.4 ± 1.8 cm/sec | 49.7 ± 1.5 cm/sec |
| Anodal Monophasic | | |
| 48.1 ± 1.2 cm/sec | 51.8 ± 0.5 cm/sec | 54.9 ± 0.7 cm/sec |
| Leading Cathodal Biphasic | | |
| 50.8 ± 0.9 cm/sec | 52.6 ± 1.1 cm/sec | 52.8 ± 1.7 cm/sec |
| Leading Anodal Biphasic | | |
| 52.6 ± 2.5 cm/sec | 55.3 ± 1.5 cm/sec | 54.2 ± 2.3 cm/sec |

The differences in conduction velocities between the cathodal monophasic, anodal monophasic, leading cathodal biphasic and leading anodal biphasic were found to be significant ($p<0.001$). From the transmembrane potential measurements, the maximum upstroke ($(dV/dt)max$) of the action potentials was found to correlate well with the changes in conduction velocity in the longitudinal direction. For a four volt pulse of two millisecond duration, $(dV/dt)$ max was 63.5±2.4 V/sec for cathodal and 75.5±5.6 V/sec for anodal pulses.

EXAMPLE 2

Figure 6:
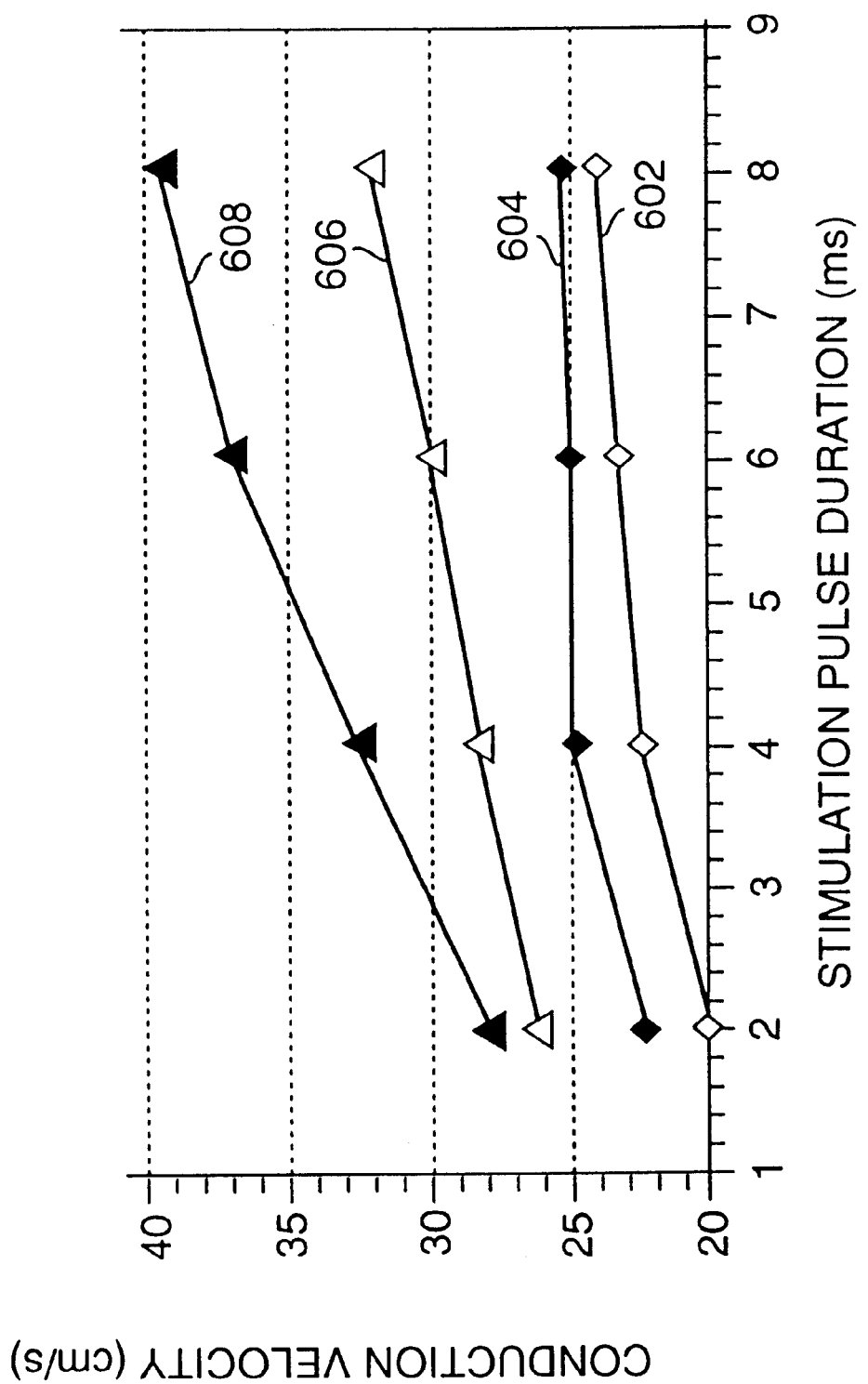
FIG. 6 graphs conduction velocity transverse to the fiber vs. pacing duration resulting from leading anodal biphasic pulse.
Figure 7:
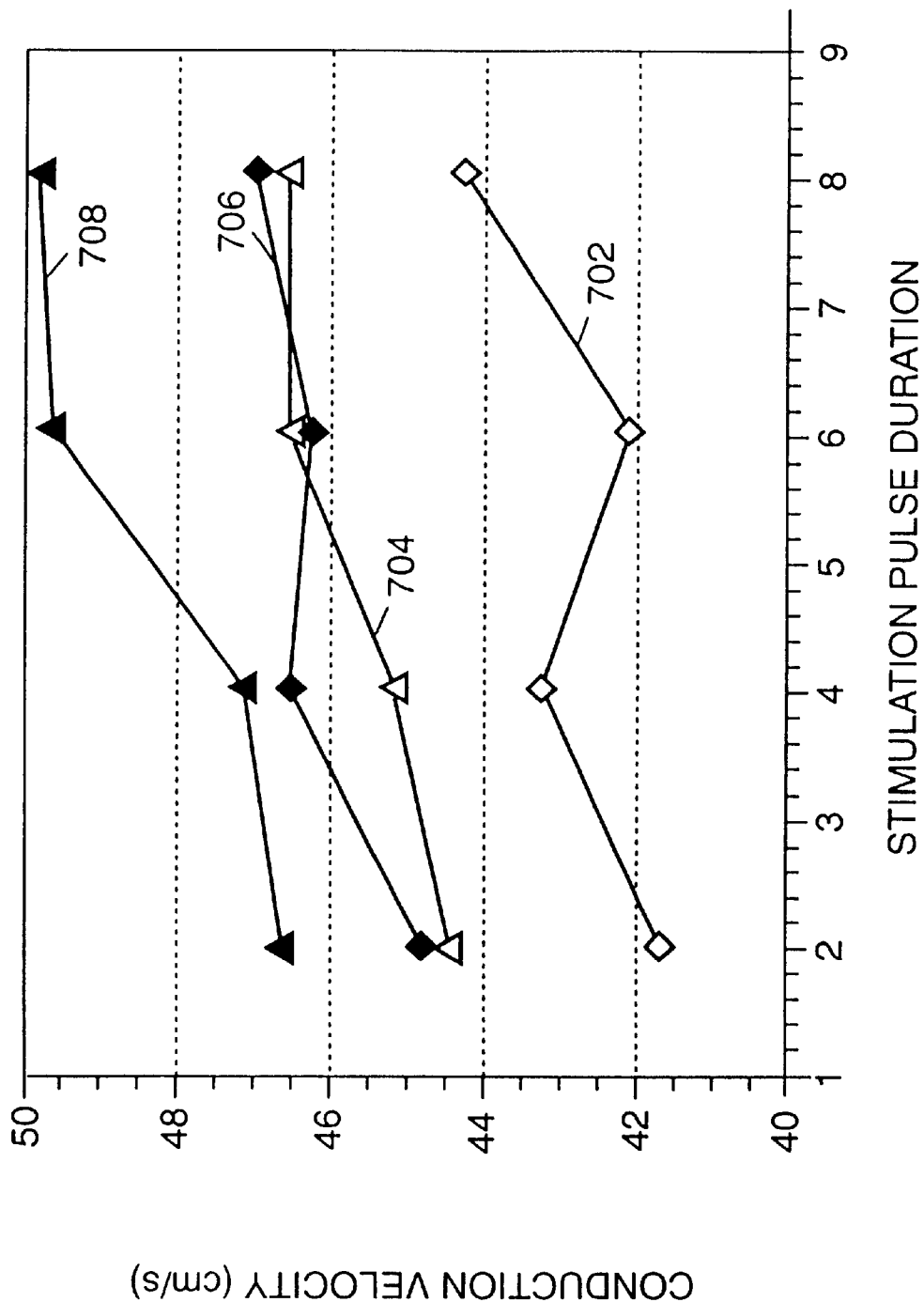
FIG. 7 graphs conduction velocity parallel to the fiber vs. pacing duration resulting from leading anodal biphasic pulse.

The effects of varying pacing protocols on cardiac electrophysiology were analyzed using Langendorff prepared isolated rabbit hearts. Stimulation was applied to the heart at a constant voltage rectangular pulse. The following protocols were examined: monophasic anodal pulse, monophasic cathodal pulse, leading anodal biphasic pulse, and leading cathodal biphasic pulse. Administered voltage was increased in one volt steps from one to five volts for both anodal and cathodal stimulation. Duration was increased in two millisecond steps from two to ten milliseconds. Epicardial conduction velocities were measured along and transverse to the left ventricular fiber direction at a distance between three to six millimeters from the left ventricular free wall. FIGS. 6 and 7 depict the effects of stimulation pulse duration and the protocol of stimulation administered on the conduction velocities.

FIG. 6 depicts the velocities measured between three millimeters and six millimeters transverse to the fiber direction. In this region, cathodal monophasic stimulation 602 demonstrates the slowest conduction velocity for each stimulation pulse duration tested. This is followed by anodal monophasic stimulation 604 and leading cathodal biphasic stimulation 606. The fastest conduction velocity is demonstrated by leading anodal biphasic stimulation 608.

FIG. 7 depicts the velocities measured between three millimeters and six millimeters parallel to the fiber direction. In this region, cathodal monophasic stimulation 702 demonstrates the slowest conduction velocity for each stimulation pulse duration tested. Velocity results of anodal monophasic stimulation 704 and leading cathodal biphasic stimulation 706 are similar to those with anodal monophasic stimulation, but demonstrating slightly quicker speeds. The fastest conduction velocity is demonstrated by leading anodal biphasic stimulation 708.

Figure 8:
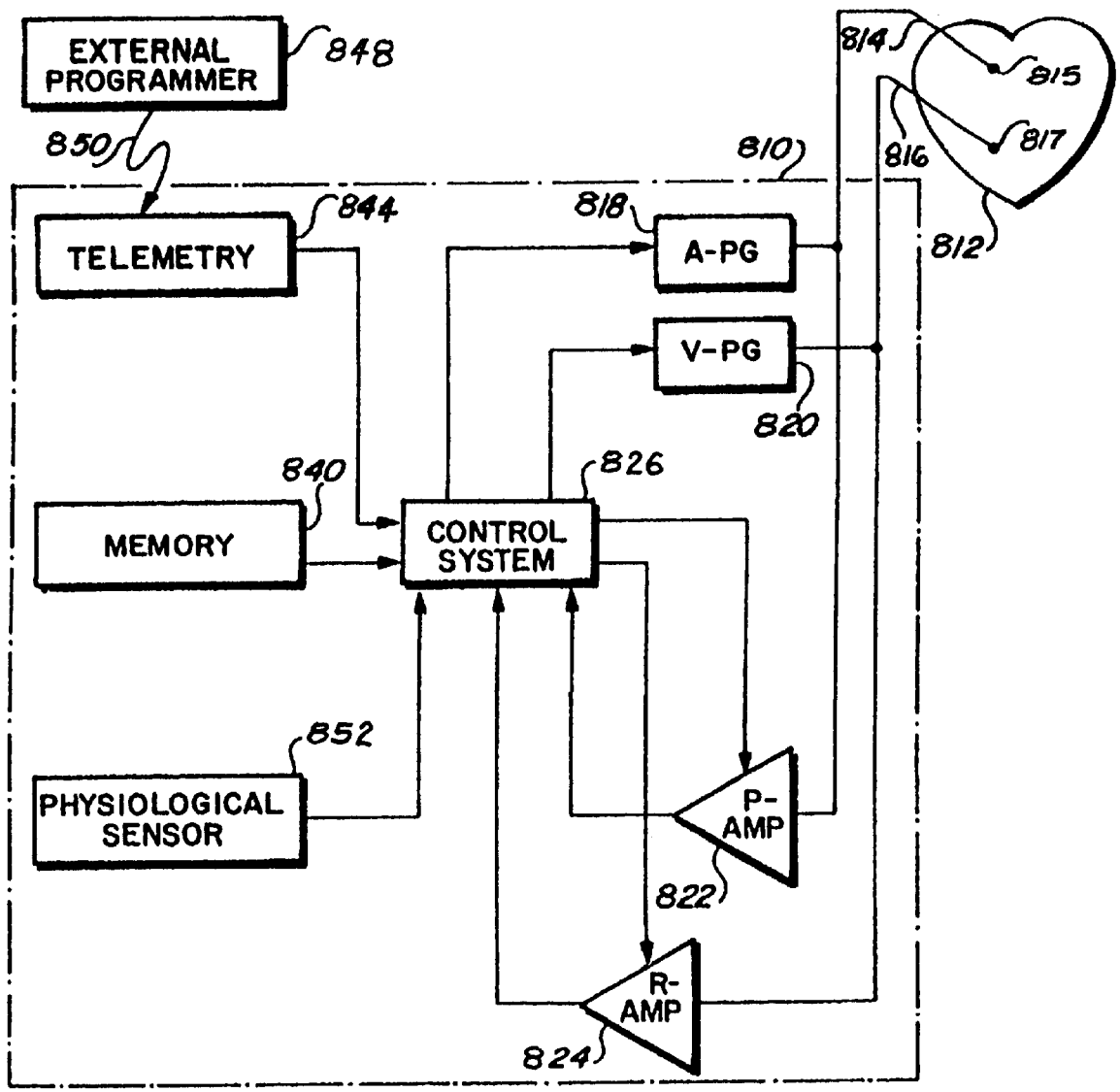
FIG. 8 illustrates a schematic view of a cardiac stimulator according to one embodiment of the present invention.

Referring then to FIG. 8, a block diagram of a dual-chamber pacemaker 810 is illustrated. The pacemaker 810 is coupled to a heart 812 by way of leads 814 and 816. The lead 814 has an electrode 815 that is in contact with one of the atria of the heart, and the lead 816 has an electrode 817 that is in contact with one of the ventricles of the heart. The leads 814 and 816 carry stimulating pulses to the electrodes 815 and 817 from an matrial pulse generator (A-PG) 818 and a ventricular pulse generator (V-PG) 820, respectively. Further, electrical signals from the atria are carried from the electrode 815, through the lead 814, to the input terminal of an atrial channel sense amplifier (P-AMP) 822; and electrical signals from the ventricles are carried from the electrode 817, through the lead 816, to the input terminal of a ventricular sense channel amplifier (R-AMP) 824.

A control circuit or control system 826 controls the dual-chamber pacer 810. The control system 826 receives the output signals from the atrial amplifier 822, as well as the output signals from the ventricular amplifier 824. The output signals at the outputs of the atrial amplifier 822 and the ventricular amplifier 824 are generated each time that a P-wave or an R-wave, respectively, is sensed within the heart 812. The control circuit or system 826 also generates trigger signals that are sent to the atrial pulse generator 818 and the ventricular pulse generator 820. These trigger signals are generated each time that a stimulation pulse is to be generated by the respective pulse generator 818 or 820. A stimulation pulse generated by the A-PG 818 is referred to as the "A-pulse," and the stimulation pulse generated by the V-PG 820 is referred to as the "V-pulse." During the time that either an A-pulse or V-pulse is being delivered to the heart, the corresponding amplifier, P-AMP 822 and/or R-AMP 824, is typically disabled by way of a blanking signal presented to these amplifiers from the control system. This blanking action prevents the amplifiers 822 and 824 from becoming saturated from the relatively large A-pulse or V-pulse, respectively, that is present at the input terminals of such amplifiers during this time. Such blanking action also prevents the sensing of residual electrical signals that may be present in the muscle tissue as a result of the pacer stimulation, which sensing could falsely be interpreted as P-waves or R-waves.

Referring further to FIG. 8, the pacer 810 also includes a memory circuit 840 that is coupled to the control system

826. The memory circuit 840 allows certain control parameters, used by the control system 826 in controlling the operation of the pacemaker, to be programmably stored and modified, as required, in order to customize the pacer's operation to suit the needs of a particular patient. Such data includes the basic timing intervals used during operation of the pacemaker, initial pacing rate, minimum pacing rate, and the programmed atrial escape interval. Further, data sensed during the operation of the pacer may be stored in the memory 840 for later retrieval and analysis.

A telemetry circuit 844 is optionally included in the pacer 810. This telemetry circuit 844 is connected to the control system 826 to provide a data link external to the body. The telemetry circuit 844, which is internal to the implantable pacer 810, may be selectively coupled to an external programming device 848 by means of an appropriate communication link 850, which communication link 850 may be any suitable electromagnetic link, such as an RF (radio frequency) channel or an optical channel. Advantageously, through the external programmer 848 and the communication link 850, desired commands may be sent to the control system 826. Similarly, through this communication link 850 and the programmer 848 data (either held within the control system 826, as in a data latch, or stored within the memory 840) may be remotely received from the pacer 810. In this manner, non-invasive communications can be established from time to time with the implanted pacer 810 from a remote, non-implanted.

The pacer 810 in FIG. 8 may be embodied with any number of atrial pulse generators or ventricular pulse generators as suit the pacing needs of a given patient.

In accordance with an alternate embodiment of the present invention, the pacemaker 810 may further include one or more physiological sensors 852 (including physiological parameter sensor circuitry) that are connected to the control system 826. While the sensor 852 is illustrated in FIG. 8 as being included within the pacer 810, it is to be understood that the sensor may also be external to the pacer 810, yet still be implanted within or carried by the patient. A common type of sensor is an activity sensor, such as a piezoelectric crystal, mounted to the case of the pacemaker. Other types of sensors, such as physiologic sensors that sense the oxygen content of blood, respiration rate, pH of blood, and the like, may also be used in lieu of, or in addition to, an activity sensor. The type of sensor, if any, used is not critical to the present invention. Any sensor or combination of sensors capable of sensing body motion or a physiological parameter relatable to the rate at which the heart should be beating can be used. The use of such sensors makes the pacemaker rate-responsive, because the pacemaker adjusts the rate of pacing in a manner that tracks the physiological needs of the patient.

In one aspect of the invention, electrical stimulation is administered to the cardiac muscle. The anodal stimulation component of biphasic electrical stimulation augments cardiac contractility by hyperpolarizing the tissue prior to excitation, leading to faster impulse conduction, more intracellular calcium release, and the resulting superior cardiac contraction. The cathodal stimulation component eliminates the drawbacks of anodal stimulation, resulting in effective cardiac stimulation at a lower voltage level than would be required with anodal stimulation alone. This, in turn, extends pacemaker battery life and reduces tissue damage.

In a second aspect of the invention, biphasic electrical stimulation is administered to the cardiac blood pool, that is, the blood entering and surrounding the heart. This enables cardiac stimulation without the necessity of placing electrical leads in intimate contact with cardiac tissue, thereby diminishing the likelihood of damage to this tissue. The stimulation threshold of biphasic stimulation administered via the blood pool is in the same range as standard stimuli delivered directly to the heart muscle. Through the use of biphasic electrical stimulation to the cardiac blood pool it is therefore possible to achieve enhanced cardiac contraction, without skeletal muscle contraction, cardiac muscle damage or adverse effects to the blood pool.

In a third aspect of the invention, biphasic electrical stimulation is applied to striated (skeletal) muscle tissue. The combination of anodal with cathodal stimulation results in the contraction of a greater number of muscle motor units at lower levels of voltage and/or electrical current, resulting in improved muscle response. The benefits of the present invention are realized both when there is direct stimulation, as well as when the stimulation is indirect (through the skin). Benefits may be realized in physical therapy and muscle rehabilitation contexts, for example, stimulation of muscles over time while waiting for damaged nerves to regenerate.

In a fourth aspect of the invention, biphasic electrical stimulation is applied to smooth muscle tissue. Visceral smooth muscle is found in the walls of hollow visceral organs such as the stomach, intestines, urinary bladder and uterus. The fibers of smooth muscles are capable of stimulating each other. Thus, once one fiber is stimulated, the depolarization wave moving over its surface may excite adjacent fibers, which in turn stimulate still others. Benefits of such stimulation can be realized, for example, in situations where incontinence has been caused by trauma or disease.

Having thus described the basic concept of the invention, it will be readily apparent to those skilled in the art that the foregoing detailed disclosure is intended to be presented by way of example only, and is not limiting. Various alterations, improvements and modifications will occur and are intended to those skilled in the art, but are not expressly stated herein. These modifications, alterations and improvements are intended to be suggested hereby, and within the scope of the invention. Further, the stimulating pulses described in this specification are well within the capabilities of existing electronics with appropriate programming. Biphasic stimulation as provided by the present invention may be desirable in additional situations where electrical stimulation is indicated; such as, nerve tissue stimulation and bone tissue stimulation. Accordingly, the invention is limited only by the following claims and equivalents thereto.

What is claimed is:

1. An apparatus for stimulating muscle tissue with biphasic waveforms, comprising:

pulse generation electronics that generate a pulse, the pulse defining a first stimulation phase and defining a second stimulation phase, wherein the first stimulation phase has a first phase polarity, a first phase amplitude, a first phase shape, and a first phase duration for preconditioning the muscle tissue to accept subsequent stimulation, and wherein the second stimulation phase has a polarity opposite to the first phase polarity, a second phase amplitude that is larger in absolute value than the first phase amplitude, a second phase shape, and a second phase duration; and leads connected to the pulse generation electronics and being adapted to apply the first stimulation phase and the second stimulation phase in sequence to the muscle tissue, wherein the muscle tissue is selected from the group consisting of striated muscle, smooth muscle and mixed muscle;

wherein the first phase amplitude is ramped from a baseline value to a second value.

2. An apparatus for stimulating muscle tissue with biphasic waveforms, comprising:

pulse generation electronics that generate a pulse, the pulse defining a first stimulation phase and defining a second stimulation phase, wherein the first stimulation phase has a first phase polarity, a first phase amplitude, a first phase shape, and a first phase duration for preconditioning the muscle tissue to accept subsequent stimulation, and wherein the second stimulation phase has a polarity opposite to the first phase polarity, a second phase amplitude that is larger in absolute value than the first phase amplitude, a second phase shape, and a second phase duration; and leads connected to the pulse generation electronics and being adapted to apply the first stimulation phase and the second stimulation phase in sequence to the muscle tissue, wherein the muscle tissue is selected from the group consisting of striated muscle, smooth muscle and mixed muscle;

wherein the first phase amplitude is ramped from a baseline value to a second value, and wherein the absolute value of the second value is equal to the absolute value of the second phase amplitude.

3. An apparatus for stimulating muscle tissue with biphasic waveforms, comprising:

pulse generation electronics that generate a pulse, the pulse defining a first stimulation phase and defining a second stimulation phase, wherein the first stimulation phase has a first phase polarity, a first phase amplitude, a first phase shape, and a first phase duration for preconditioning the muscle tissue to accept subsequent stimulation, and wherein the second stimulation phase has a polarity opposite to the first phase polarity, a second phase amplitude that is larger in absolute value than the first phase amplitude, a second phase shape, and a second phase duration; and leads connected to the pulse generation electronics and being adapted to apply the first stimulation phase and the second stimulation phase in sequence to the muscle tissue, wherein the muscle tissue is selected from the group consisting of striated muscle, smooth muscle and mixed muscle;

wherein the first stimulation phase further comprises a series of stimulating pulses of a predetermined amplitude, polarity, and duration.

4. An apparatus for stimulating muscle tissue with biphasic waveforms, comprising:

pulse generation electronics that generate a pulse, the pulse defining a first stimulation phase and defining a second stimulation phase, wherein the first stimulation phase has a first phase polarity, a first phase amplitude, a first phase shape, and a first phase duration for preconditioning the muscle tissue to accept subsequent stimulation, and wherein the second stimulation phase has a polarity opposite to the first phase polarity, a second phase amplitude that is larger in absolute value than the first phase amplitude, a second phase shape, and a second phase duration; and leads connected to the pulse generation electronics and being adapted to apply the first stimulation phase and the second stimulation phase in sequence to the muscle tissue, wherein the muscle tissue is selected from the group consisting of striated muscle, smooth muscle and mixed muscle;

wherein the first phase polarity is positive and the maximum subthreshold amplitude is about 0.5 to 3.5 volts.

5. An apparatus for stimulating muscle tissue with biphasic waveforms, comprising:

pulse generation electronics that generate a pulse, the pulse defining a first stimulation phase and defining a second stimulation phase, wherein the first stimulation phase has a first phase polarity, a first phase amplitude, a first phase shape, and a first phase duration for preconditioning the muscle tissue to accept subsequent stimulation, and wherein the second stimulation phase has a polarity opposite to the first phase polarity, a second phase amplitude that is larger in absolute value than the first phase amplitude, a second phase shape, and a second phase duration; and leads connected to the pulse generation electronics and being adapted to apply the first stimulation phase and the second stimulation phase in sequence to the muscle tissue, wherein the muscle tissue is selected from the group consisting of striated muscle, smooth muscle and mixed muscle;

wherein the first phase duration is at least as long as the second phase duration and the first phase duration is about one to nine milliseconds.

6. An apparatus for stimulating muscle tissue with biphasic waveforms, comprising:

pulse generation electronics that generate a pulse, the pulse defining a first stimulation phase and defining a second stimulation phase, wherein the first stimulation phase has a first phase polarity, a first phase amplitude, a first phase shape, and a first phase duration for preconditioning the muscle tissue to accept subsequent stimulation, and wherein the second stimulation phase has a polarity opposite to the first phase polarity, a second phase amplitude that is larger in absolute value than the first phase amplitude, a second phase shape, and a second phase duration; and leads connected to the pulse generation electronics and being adapted to apply the first stimulation phase and the second stimulation phase in sequence to the muscle tissue, wherein the muscle tissue is selected from the group consisting of striated muscle, smooth muscle and mixed muscle;

wherein the first phase duration is at least as long as the second phase duration and the second phase duration is about 0.2 to 0.9 millisecond.

7. An apparatus for stimulating muscle tissue with biphasic waveforms, comprising:

pulse generation electronics that generate a pulse, the pulse defining a first stimulation phase and defining a second stimulation phase, wherein the first stimulation phase has a first phase polarity, a first phase amplitude, a first phase shape, and a first phase duration for preconditioning the muscle tissue to accept subsequent stimulation, and wherein the second stimulation phase has a polarity opposite to the first phase polarity, a second phase amplitude that is larger in absolute value than the first phase amplitude, a second phase shape, and a second phase duration; and leads connected to the pulse generation electronics and being adapted to apply the first stimulation phase and the second stimulation phase in sequence to the muscle tissue, wherein the muscle tissue is selected from the group consisting of striated muscle, smooth muscle and mixed muscle;

wherein the second phase amplitude is about two volts to twenty volts.

8. An apparatus for stimulating muscle tissue with biphasic waveforms, comprising:

pulse generation electronics that generate a pulse, the pulse defining a first stimulation phase and defining a second stimulation phase, wherein the first stimulation phase has a first phase polarity, a first phase amplitude, a first phase shape, and a first phase duration for preconditioning the muscle tissue to accept subsequent stimulation, and wherein the second stimulation phase has a polarity opposite to the first phase polarity, a second phase amplitude that is larger in absolute value than the first phase amplitude, a second phase shape, and a second phase duration; and leads connected to the pulse generation electronics and being adapted to apply the first stimulation phase and the second stimulation phase in sequence to the muscle tissue, wherein the muscle tissue is selected from the group consisting of striated muscle, smooth muscle and mixed muscle;

wherein the second phase duration is less than 0.3 milliseconds and the second phase amplitude is greater than twenty volts.

9. An apparatus for stimulating muscle tissue with biphasic waveforms, comprising:

pulse generation electronics that generate a pulse, the pulse defining a first stimulation phase and defining a second stimulation phase, wherein the first stimulation phase has a first phase polarity, a first phase amplitude, a first phase shape, and a first phase duration for preconditioning the muscle tissue to accept subsequent stimulation, and wherein the second stimulation phase has a polarity opposite to the first phase polarity, a second phase amplitude that is larger in absolute value than the first phase amplitude, a second phase shape, and a second phase duration; and leads connected to the pulse generation electronics and being adapted to apply the first stimulation phase and the second stimulation phase in sequence to the muscle tissue, wherein the muscle tissue is selected from the group consisting of striated muscle, smooth muscle and mixed muscle;

wherein the stimulation to the muscle is selected from the group consisting of direct stimulation to the muscle and indirect stimulation to the muscle; and wherein the indirect stimulation is administered through skin.

10. An apparatus for stimulating muscle tissue with biphasic waveforms, comprising:

pulse generation electronics that generate a pulse, the pulse defining a first stimulation phase and defining a second stimulation phase;

wherein the first stimulation phase has a positive polarity, a first phase amplitude, a first phase shape, and a first phase duration, where the first phase amplitude is about 0.5 to 3.5 volts, and the first phase duration is about one to nine milliseconds; and wherein the second stimulation phase has a negative polarity, a second phase amplitude that is larger in absolute value than the first phase amplitude, a second phase shape, and a second phase duration, where the second phase amplitude is about two volts to twenty volts, and the second phase duration is about 0.2 to 0.9 millisecond; and leads connected to the pulse generation electronics and being adapted to apply the first stimulation phase and the second stimulation phase in sequence to the muscle tissue, wherein the muscle tissue is selected from the group consisting of striated muscle, smooth muscle and mixed muscle, and wherein the stimulation to the muscle is selected from the group consisting of direct stimulation to the muscle and indirect stimulation to the muscle.

* * * * *